United States Patent
Strey et al.

(10) Patent No.: US 10,427,160 B2
(45) Date of Patent: Oct. 1, 2019

(54) RAPID AND CONTINUOUS ANALYTE PROCESSING IN DROPLET MICROFLUIDIC DEVICES

(71) Applicant: The Research Foundation for The State University of New York, Albany, NY (US)

(72) Inventors: Helmut Strey, Stony Brook, NY (US);
Robert Kimmerling, Shirley, NY (US);
Tomasz Bakowski, Levittown, NY (US)

(73) Assignee: The Research Foundation for The State University of New York, Albany, NY (US)

(*) Notice: Subject to any disclaimer, the term of this patent is extended or adjusted under 35 U.S.C. 154(b) by 0 days.

(21) Appl. No.: 15/908,453

(22) Filed: Feb. 28, 2018

(65) Prior Publication Data
US 2018/0250678 A1  Sep. 6, 2018

Related U.S. Application Data

(60) Continuation of application No. 15/457,459, filed on Mar. 13, 2017, which is a division of application No. 12/875,914, filed on Sep. 3, 2010, now Pat. No. 9,625,454.

(60) Provisional application No. 61/240,188, filed on Sep. 4, 2009.

(51) Int. Cl.
| | |
|---|---|
| *C12Q 1/68* | (2018.01) |
| *B01L 3/00* | (2006.01) |
| *G01N 33/543* | (2006.01) |
| *C12Q 1/686* | (2018.01) |
| *C12N 15/10* | (2006.01) |
| *B01L 7/00* | (2006.01) |

(52) U.S. Cl.
CPC ..... *B01L 3/502784* (2013.01); *B01L 3/50273* (2013.01); *B01L 3/502715* (2013.01); *B01L 3/502761* (2013.01); *B01L 3/502776* (2013.01); *C12N 15/1096* (2013.01); *C12Q 1/686* (2013.01); *G01N 33/54313* (2013.01); *G01N 33/54326* (2013.01); *G01N 33/54366* (2013.01); *B01L 7/52* (2013.01); *B01L 2200/0647* (2013.01); *B01L 2200/0673* (2013.01); *B01L 2300/0864* (2013.01); *B01L 2400/043* (2013.01); *B01L 2400/0487* (2013.01)

(58) Field of Classification Search
None
See application file for complete search history.

(56) References Cited

PUBLICATIONS

Kumaresan et al. (Anal Chem, 2008, 80, 3522-3529) (Year: 2008).*
Liu et al (Trends in Biotechnology, 2009, 27(10):572-580) (Year: 2009).*
Hamaguchi et al. (Clinical Chemistry, 1998, 44(11):2256-2263) (Year: 1998).*

* cited by examiner

*Primary Examiner* — Stephanie K Mummert
(74) *Attorney, Agent, or Firm* — Scully, Scott, Murphy & Presser, P.C.

(57) ABSTRACT

The compositions and methods described herein are designed to introduce functionalized microparticles into droplets that can be manipulated in microfluidic devices by fields, including electric (dielectrophoretic) or magnetic fields, and extracted by splitting a droplet to separate the portion of the droplet that contains the majority of the microparticles from the part that is largely devoid of the microparticles. Within the device, channels are variously configured at Y- or T junctions that facilitate continuous, serial isolation and dilution of analytes in solution. The devices can be limited in the sense that they can be designed to output purified analytes that are then further analyzed in separate machines or they can include additional channels through which purified analytes can be further processed and analyzed.

11 Claims, 5 Drawing Sheets

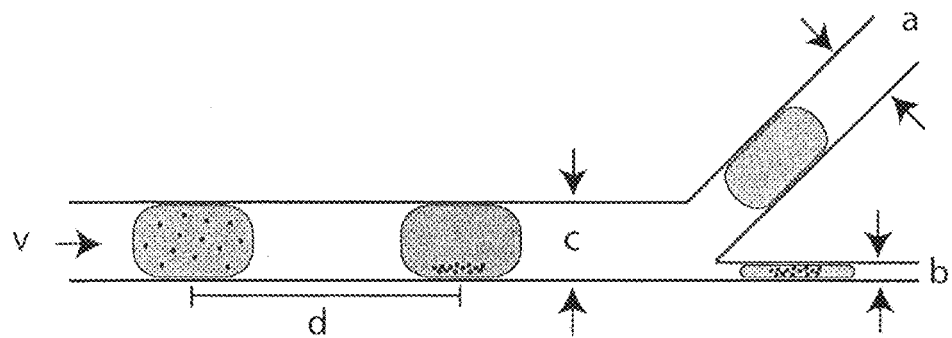

FIG. 2A

Device Parameter Ranges

| Waste channel diameter (a) | 1 μm – 1 mm |
|---|---|
| Harvesting channel diameter (b) | 1 μm – 1 mm |
| Main channel diameter (c) | 2 μm – 1 mm |
| Droplet Frequency (f) | Up to 10 kHz |
| Flow Velocity (v) | nanoliter/sec – milliliter/sec |
| Droplet volume (dv) | picoliter to microliter |
| Separation accuracy | Better than 1% |
| Number of beads | Up to 1000 |

*Flow velocity depends on the desired frequency of droplets as well as the desired center-to-center distance between these droplets

FIG. 2B

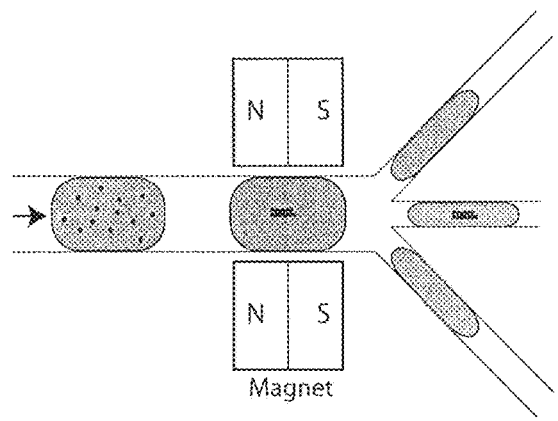

FIG. 3

Mean =93.17
Std. Dev. =5.292
N =100

Mean =375.61
Std. Dev. =23.93
N =100

RAPID AND CONTINUOUS ANALYTE PROCESSING IN DROPLET MICROFLUIDIC DEVICES

REFERENCE TO RELATED APPLICATIONS

This application is a continuation of co-pending U.S. application Ser. No. 15/457,459, filed Mar. 13, 2017, which is a division of U.S. application Ser. No. 12/875,914, filed Sep. 3, 2010, now U.S. Pat. No. 9,625,454, which claims the benefit of U.S. Provisional Application No. 61/240,188, filed Sep. 4, 2009, each of which is hereby incorporated by reference in its entirety.

STATEMENT REGARDING FEDERALLY SPONSORED RESEARCH AND DEVELOPMENT

This invention was made with government support awarded by the U.S. Department of Energy under Grant No. ER46323 and the National Science Foundation under Grant No. NSF-DMR-0606282. The government has certain rights in this invention.

FIELD OF THE INVENTION

This invention relates to microfluidic devices and, more particularly, to microfluidic devices that include a field generator to manipulate tagged analytes, including nucleic acids in single cells to generate cDNA libraries. The devices can support rapid, continuous processing of analytes.

BACKGROUND

Advancements in soft-lithography and microfluidics techniques have brought the idea of lab-on-a-chip technology to the forefront of modern chemical and biomedical research (McDonald et al., Electrophoresis, 21(1):27-40, 2000).

Microfluidics improves standard laboratory protocols insofar as it allows for the manipulation of volumes on the order of picoliters, and this creates a higher degree of control and minimizes the use of costly or toxic reagents. Of particular interest has been the application of droplet or digital microfluidics, which employs the use of droplet formation and manipulation in microfluidics devices (Huebner et al., Lab on a Chip, 8:1244-1254, 2008; The et al., Lab on a Chip, 8:198-220, 2008). Droplet formation allows for the encapsulation and thus isolation of specific solutes, which greatly reduces the potential for mixing or dispersion caused by velocity gradients within the channel. Also, with high monodispersity, droplet microfluidics permits precise fusion of various solutions at specific ratios using electric fields and droplet frequency synchronization (Ahn et al., Applied Physics Letters, 88(26):265106, 2006). This level of precise control and efficiency has made droplet microfluidics devices an ideal platform for genetic analyses that would otherwise require much more costly and time consuming procedures.

SUMMARY OF THE INVENTION

The present invention is based, in part, on techniques we developed to concentrate and extract analytes using functionalized particles in droplet microfluidic devices in a continuous fashion. These methods, and the devices, compositions, and kits assembled for carrying them out, allow specific analytes to be extracted from complex mixtures inside individual droplets, and subsequent analysis is facilitated by continuous, rapid movement of the droplets through microfluidic devices. The extraction is facilitated by the formation of a complex between the analyte and a functionalized particle such as a microsphere or nanotube assembly that carries a tag that specifically binds the analyte. The particle is, furthermore, responsive to a field within the device (e.g., a magnetic or electric field). For example, complexes that include magnetized microspheres or nanotubes can be directed to one side of a droplet or another with a magnet (e.g., an embedded rare-earth magnet). Alternatively, complexes having dielectric particles can be marginalized using a dielectrophoretic force. Thus, the field generator can be an electrode emitting an oscillating electric field gradient and the functionalized particle can include a dielectric microsphere or nanotube assembly. In other embodiments, the field generator can be a focused light or laser beam. In that case, the functionalized particle can include a dielectric microsphere or nanotube assembly. To reflect the presence of a tag (which we may also refer to as an analyte-specific moiety) as well as the responsiveness to a field, we may refer to the functionalized particle as a field-responsive tag.

The microfluidic devices include channels through which a plurality of droplets may travel; one or more field generators that attract or repel complexes within the droplets; and, optionally, one or more pairs of electrodes that destabilize the droplets and thereby facilitate their coalescence. More specifically, the devices include a series of contiguous channels that intersect at certain points with one another at variously shaped junctions (e.g., at T-, W-, X-, or Y-shaped junctions) and a field generator such as a rare-earth magnet. The field generation (e.g., magnet) can be positioned such that it generates a field perpendicular to or parallel to a channel and the fluid flow within it. Exemplary arrangements of channels, with the magnetic moment applied perpendicular to and parallel to the fluid flow direction are shown in FIGS. 1A-1D, and a series of photomicrographs showing bead-containing droplets moving through devices configured in these ways are shown in FIGS. 8 and 9.

At some points in the device, the channels may be contiguous with one another, with no significant structural difference between the terminal segment of one channel and the initial segment of the next. At other points in the device, the channels may form a junction to allow for continuous, serial separation and dilution of analytes. For example, a first channel may divide into two; into a second channel and a third channel, thereby forming a Y- or T-shaped junction. In other embodiments, a first channel may divide into more than two channels (e.g., three, four, five, or more channels). Where a droplet traveling through the first channel confronts a junction, it may be partitioned such that a portion of the droplet proceeds down each newly confronted channel. For example, at a Y-shaped junction, a portion of the droplet can proceed through the second channel and the remainder of the droplet can proceed down the third channel. At a W-shaped junction, a portion of the droplet can proceed through each of three channels, as shown in FIG. 3, where the droplet passes between a pair of field generators adjacent the channel. Where the analyte has been marginalized within the droplet due to association with a field-responsive tag, the analyte becomes more concentrated in the channel receiving the portion of the droplet having the majority of the analyte. Junctions (e.g., T- and X-shaped junctions) are also useful in merging droplets. A droplet traveling through a first channel and a droplet traveling through a second channel can, upon passing through a junction and entering a third channel, coalesce in the third channel. As noted, the junctions within the present devices can be variously shaped and include junctions in a T-, W-, X-, or Y-shape. Generally, the junctions unite three or more channels, with junctions such as the W- and Y-shaped junctions illustrated herein being useful in splitting droplets and junctions such as T- and X-shaped junctions being useful in coalescing droplets and encapsulating cells or other analytes. Where the droplet traveling through the first channel includes an analyte and the droplet traveling through the second channel includes an analyte-free solution (e.g., a buffer), the analyte is diluted when the droplets coalesce. The angles of the channels forming a junction can vary and, as indicated, where right angles are formed, the junction can assume a common X- or T-shape. The diameter of the channels extending from a junction can also either be the same or different. In particular, the channels into which a droplet is split can be the same size or different (e.g., the channel receiving the portion of the droplet that carries the majority of the analyte can be smaller than the channel that receives the remainder of the droplet). When expressed as a ratio, the diameter of a first channel relative to the diameter of a second channel can be at least or about 10:1 to about 1:1 (e.g., 10:2, 10:3.33 or 10:5). The first channel can be a channel prior to a junction and the second channel can be a channel past a junction. Alternatively, the first and second channels can be channels past the junction. The determination of "prior to" and "past" can be determined by the direction of fluid flow and/or the movement of a droplet through the device.

Thus, in one aspect, the invention features microfluidic devices that include (a) a substrate comprising a series of contiguous channels and (b) a field generator, wherein the series of contiguous channels includes a first channel having an initial segment configured to receive a droplet comprising an analyte that is bound to a functionalized particle (the tagged droplet), a middle segment along which the tagged droplet travels, and a terminal segment that bifurcates into a plurality of channels (e.g., into a second channel and a third channel). The field generator is positioned adjacent to the first channel (e.g., adjacent to the middle segment of the first channel and/or just prior to the junction) and marginalizes the analyte toward a side of the tagged droplet (either toward or away from the field generator) such that, upon reaching the junction (e.g., the point where the first channel bifurcates), a portion of the tagged droplet that includes the majority of the analyte enters the second channel and the remainder of the tagged droplet enters the third channel, thereby producing, in the second channel, a smaller droplet that contains the majority of the analyte while excluding at least some of the complex mixture. On occasion, we may refer to the microfluidic devices described herein more simply as "chips."

Suitable substrates will be known to those of ordinary skill in the art and include silicon, polydimethylsiloxane, glass, and molded plastic (e.g., poly(styrene)).

The inventions described herein can be used in any instance where it is desirable to extract an analyte from a complex mixture (e.g., a cell lysate or an environmental sample) into a cleaner environment for processing and analysis. The microfluidic devices can be used, for example, to extract any biomolecule for which a functionalized particle can be created. While the process may be limited to extraction, the microfluidic devices can be configured such that an extracted analyte is further processed within the device. Moreover, the further processing can include multiple steps. For example, a single droplet microfluidic device can be used to extract, amplify, and quantitate the amount of a particular nucleic acid within a biological cell. While analytes are described further below, we note in the context of this example that the nucleic acid can be DNA or RNA (e.g., mRNA or microRNA) that naturally exists within a cell (e.g., a cancerous cell) or DNA or RNA that is introduced into a cell (e.g., a transgene or oligonucleotide, including an antisense oligonucleotide or an oligonucleotide that facilitates RNAi (e.g., an siRNA)).

The microfluidic devices per se can be fabricated using standard soft-lithography techniques. Exemplary fabrication processes are described further below and can be used in making the devices of the present invention. One of ordinary skill in the art will be familiar with fabrication methods and further understand that the precise geometry of the devices described herein can vary. For example, the devices can include one or a plurality of field generators. For example, one field generator (e.g., a magnet) can be positioned adjacent to each channel in which an analyte-containing droplet travels before being split in two. Where there are one, two, three, or four (or more) channels, there can be one, two, three, or four (or more) corresponding field generators. Alternatively, one, two, three, or four (or more) channels can be arranged so that each channel passes the same field generator. The process of marginalizing a complex (comprising a functionalized microparticle and an analyte), splitting a droplet comprising the marginalized analyte, and re-diluting the split droplet can be repeated as many times as necessary for sufficient buffer exchange. We anticipate diluting an analyte by a factor of at least or about 5-15 at each pass. By way of illustration, if the original droplet is about 150 µm in diameter, and a 10 µm droplet is extracted from the original droplet, the dilution factor is 15.

The key events that can occur within the present devices include droplet plug formation (e.g., the formation of an "original" or unreacted droplet), droplet plug split, and droplet coalescence. As noted, droplets containing magnetic beads can be split into channels of unequal widths or diameters. When there is no magnet embedded, the beads show no bias to either the larger or the smaller diameter channel. In contrast, in the presence of a magnetic field, the beads are strongly attracted to the magnet and thus split into the smaller diameter channel. The use of two field generators can propel a tagged analyte toward the center of droplet, in which case it may enter a central passage at a radial division, such as the W-shaped junction illustrated in FIG. 3.

The device per se, any of the peripheral components that control the flow of liquids through the device, and/or any of the solutions or reagents useful with the device (e.g., functionalized particles, buffers, aqueous solutions, and sheath liquids) can be variously packaged, together with instructions for use, as a kit. Kits comprising one or more of the compositions described herein are within the scope of the present invention, as are the processes or methods for making the present devices and analyzing an analyte using them.

The present compositions and methods may provide several advantages over current microfluidic technologies. In addition to the advantages mentioned above, the microchips may be reusable, as the analytes and other materials (e.g., buffers and reagents) are encapsulated in droplets throughout processing. The reactions can also be performed in sequence at high throughputs ranging from about 60-30,000 droplets per minute or more (depending on the flow velocity). Thus, even if the entire reaction sequence takes hours, a stream of finished product will become available for continuous analysis, at the initial droplet rate, as soon as the first droplet has navigated the device. Where the output will be fed into another device (e.g., a next generation sequencer), it is possible to perform a quality control check on a collection of droplets to ensure that the reactions have been performed properly before committing to the next analytical device. Our use of the droplet format further reduces contamination (by the physical and chemical isolation of the droplets from each other and the walls of the devices) and allows intricate manipulation and easy retrieval without any moving parts or elaborate automation. In combination with established reactions, our methods reliably produce cDNA libraries from single cells, and the end product of our workflow can be a re-usable emulsion in which each droplet contains the whole cDNA collection of a single cell bound to functionalized (e.g., magnetic) particles.

Our methods for generating single-cell cDNA libraries in droplets allows a high throughput approach to single cell genomic research. The present devices can be configured to generate single cell libraries by propelling droplets originally filled with a single cell through channels in which the cells are first lysed and then exposed to enzymes and other reagents to reverse transcribe cDNA from mRNA. The cDNA can then be amplified by propelling the droplets through a series of temperature-variant zones and adding, by way of the droplet merger and division techniques described herein, enzymes and other reagents that mediate PCR (the polymerase chain reaction). The cDNA can be released from the magnetic particles after a given number (e.g., 2-10) PCR cycles, and the cDNA library can be recovered by simply separating the magnetic beads from the amplified CAN. The separation step regenerates the initial cDNA library, which can be reused. The cDNA library, whether in a microfluidic device or a more conventional PCR machine, can then be quantitated to determine the expression level(s) of (a) specific gene(s) of interest. As individual droplet can be recovered, these droplets can be sequentially stored in an array before performing quantitative-PCR.

The present methods are amenable to use with rare cells, including those that lack specific surface markers. One example is the circulating tumor cells (CTCs) discussed in Example 3. With the present methods, one can create single cell cNDA libraries of already enriched cells and then sort the droplets by the expression of a specific CTC marker gene as measured by PCR. After having collected enough CTCs, global gene expression methods can be applied (e.g., a gene chip or next generation sequencing).

Despite its success, current droplet microfluidics suffer from an inability to concentrate target molecules or to integrate washing steps that do not dilute the target molecules. Indeed, every reaction step adds volume to the droplets. Using the present devices, one can achieve concentrating-washing steps by encapsulating functionalized microparticles and manipulating them with external fields.

BRIEF DESCRIPTION OF THE DRAWINGS

In FIG. 1A, droplets are illustrated moving along a first channel, toward and through a Y-shaped junction, into second and third channels. The magnetic moment is perpendicular to the input flow direction in FIG. 1A. The gradient of the magnetic field strength pulls the magnetic beads down, and they form chains along the field lines. The competitive forces lead to magnetic bead arrangements that stand substantially upright, as illustrated in the schematic of FIG. 1A and shown in the photomicrograph of FIG. 1B. The magnetic moment can be arranged parallel to the input flow direction, in which case the magnetic beads are pulled down and align to form chains along the field lines (see the schematic of FIG. 1C and the photomicrograph of FIG. 1D). The input channel was 50 µm wide and 25 µm high.

FIGS. 2A and 2B illustrate device parameter ranges. FIG. 2A is a schematic drawing of a first channel, a Y-shaped junction, and the second and third channels that form past the junction. "a" represents waste channel diameter; "b" represents harvesting channel diameter; "c" represents the main (or "first") channel diameter; "d" represents droplet frequency; and "v" represents flow velocity. Illustrative ranges for these parameters are listed in the Table of FIG. 2B.

FIG. 3 is a schematic illustration of an alternative arrangement of channels within a microfluidic device of the invention. Such an arrangement will be advantageous when separating several species (in this case three) that are marginalized into different regions of the droplet. This figure only shows the magnetic particles that are marginalized into the middle.

DETAILED DESCRIPTION

Figure 1A:
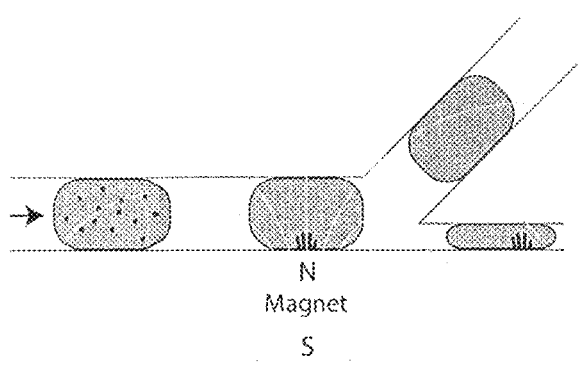
FIGS. 1A-1D constitute a panel of drawings and photomicrographs illustrating an exemplary arrangement of channels within a device of the present invention.
Figure 1B:
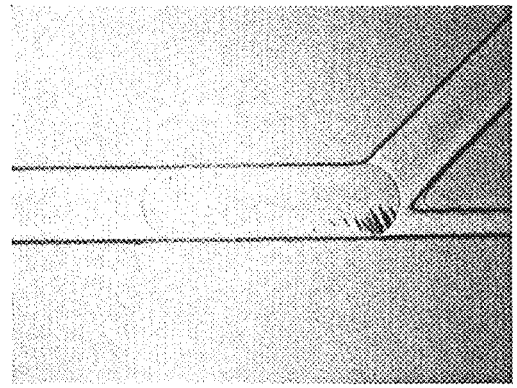
Figure 1C:
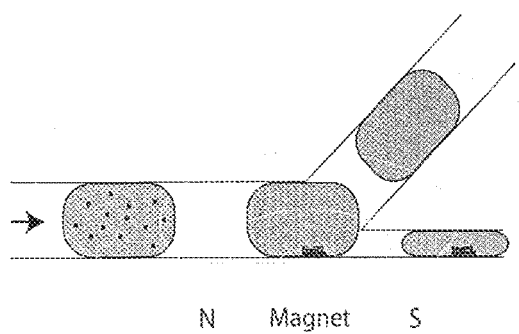
Figure 1D:
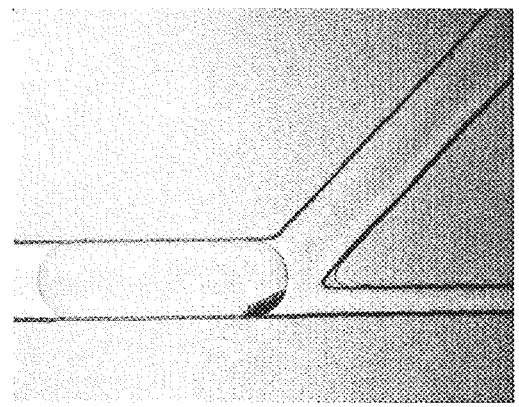
Figure 4:
FIG. 4 is a series of panels illustrating the formation of monodisperse droplets containing magnetic beads by means of a microfluidics device employing a flow focusing geometry.

To date, process steps including cell lysis, mRNA extraction, and cDNA creation and amplification with RT-PCR have been successfully completed on microfluidics devices (Morton et al., Lab on a Chip, 8(9):1448-1453, 2008; Beer et al., Analytical Chemistry, 80(6):1854-1858, 2008; Marcus et al., Analytical Chemistry, 78(3):956-958, 2006). However, previous designs have either extracted mRNA from several cells continuously or from a single cell but not at high enough throughput to address gene expression in heterogeneous cell populations. Such specificity will become increasingly important in understanding gene regulation, cell differentiation, and the development of disease states.

Recently, a new method for effectively isolating a single cell per droplet was described (Edd et al., Lab on a Chip, 8(8):1262-1264, 2008), thus eliminating the reliance on careful sample dilutions and Poisson distributions. Such droplets can be used for high throughput genetic studies by continuously merging them with droplets of other reagents to lyse the cells, collect their genetic material, and amplify the cDNA for further sequencing and analysis. To date, however, we are aware of no methods for reducing the volume of a droplet while maintaining the majority of the genetic material to be analyzed, particularly in devices that allow for continuous and rapid analysis of analytes in moving droplets; in prior methods, the volume has been increased by combining droplets containing different reagents and/or the volume has been reduced in static or surface-bound droplets. This arrangement makes it difficult to remove any unwanted materials (e.g., cell waste or used reagents) as the reactions progress on a chip.

In contrast, our methods employ functionalized particles to marginalize an analyte (e.g., genetic material) within a droplet that is then subsequently divided (e.g., by encountering a junction such as a Y junction) so the majority of the analyte becomes contained in one of the newly formed drops (for marginalization of magnetic beads, see Wang et al., Journal of Micromechanics and Microengineering, 17(10): 2148-2156, 2007). As noted, droplets continuously and rapidly pass through the channeled devices described herein. The concentration of the analyte is then, after passing into a second channel, higher in the newly formed drop, and we may then refer to the analyte as having been isolated, purified, or extracted, and subsequent rounds of marginalization and division can produce droplets in which the analyte is further isolated, purified, or extracted. By dividing droplets and merging the resulting droplets with other droplets (e.g., droplets that are analyte-free but contain, for example, a buffer or reagent), our processes allow multi-step reactions to be carried out continuously and iteratively within a single microfluidic device. This results in effective washing and efficient reactions while maintaining a high level of control over the material being analyzed and minimizing changes in droplet volume.

With the use of functionalized particles, it is possible to bind a variety of types of analytes, including cellular mRNA. The mRNA can be reverse transcribed to generate cDNA that can then be amplified and quantitated (Chien-Ju Liu et al., Biomedical Microdevices, 11(2):11, 2008).

The timing of the entry of various droplets into the device, including the droplets that originally carry the analyte, can be controlled. Movement of the droplets within the device can vary depending on flow rate and traveling distance.

Analytes and Applications:

In one embodiment, the present compositions and methods can be used to extract, process, and analyze biomolecules from single cells. More specifically, the devices can intake, in series, hundreds of cells per second, which enables profiling of gene expression in heterogeneous cell populations as well as analysis of gene expression over time in heterogeneous or homogenous cells (e.g., in the course of a developmental process or in response to an intracellular or extracellular signal).

In particular, the present devices can be used to analyze biomolecules, including nucleic acids and proteins, from a single cell. Moreover, the devices can process at high throughput (as noted above, processing several hundred cells per second and moving droplets with cell lysates and reagents past a marker point at the rate of hundreds to thousands of cells (or droplets) per second). As a result, we can quickly establish single cell genetic profiles from heterogeneous cell populations that can be used, for example, in prognostic or diagnostic tests. For example, in a diagnostic test, one could obtain cells from a patient and determine whether those cells express a cancer-related gene. One could also analyze the level of expression in various circumstances (e.g., after the patient and/or the cells have been exposed to a therapeutic agent). The cells can be obtained by any conventional method (e.g., from a biopsy, blood sample, urine sample, and the like) and can be considered healthy or diseased (e.g., malignant) or mature or immature. For example, the present compositions and methods can be used to analyze stem cells (e.g., mesenchymal stem cells) or precursor cells at any stage of differentiation and/or in the context of any therapeutic approach. Differentiated cells can also be assessed, as can cells that are affected by a disease or disorder (e.g., malignant cells, atrophied cells, metastasizing cells, infected cells, or cells from inflamed tissue).

Cells amenable to the present methods include cells obtained from multicellular organisms (including plants (e.g., a crop plant such as corn, rice, wheat, barley, or rye) and animals (e.g., a mammal, including a human)) as well as unicellular organisms (including bacteria, yeast, and fungi) and viruses. Because the cells to be analyzed can be obtained from a single human subject or "patient," the present compositions and methods can be used in "personalized" medicine. Because unicellular organisms can also be assessed, the present methods are also applicable to methods of analyzing samples from environmental, agricultural, or industrial settings. Because viral genomes can also be assessed, the present methods are useful in essentially any analysis of a virion.

Single cell mRNA analysis is likely to become increasingly important as a tool for understanding gene regulation, cellular differentiation, and the development of disease states. For example, stem cell-based technologies may rely on understanding how and when (e.g., under what environmental circumstances) a stem cell differentiates. These determinations can be difficult to make using populations of cells, as gene expression within the population may be heterogeneous. Global gene expression analysis data is often limited because it represents the average over heterogeneous cell populations. Single cell gene expression analysis can help determine not only the degree of heterogeneity in cell populations (e.g., brain tissue and tumors) but also the sequence of gene regulation events during stem cell differentiation. Our methods, using droplet microfluidic technology, can be used as high throughput methods for the analysis of gene expression at the single cell level.

While a single analyte can be analyzed, the invention is not so limited. A number of analytes (e.g., 1-10) can be analyzed concurrently by detecting a probe (e.g., a fluorescent probe) associated with each analyte.

The term "analyte" is used herein in the conventional sense to refer to a substance that is undergoing analysis. The analyte can be a substance found in nature (e.g., a cellular component such as a nucleic acid, protein, fat, or sugar) or a synthetic compound (e.g., a polymer or an organic or inorganic small molecule used as a pharmaceutical, industrial reagent, synthetic sweetener, or fertilizer).

Alternatively, the output of the device could be the input for a next generation sequencer or other machine.

Encapsulation:

Depending on the nature of the analyte, it can be processed in an aqueous droplet (in which case it would be immersed (e.g., completely immersed) in a non-aqueous sheath liquid) or a non-aqueous droplet (in which case it would be immersed (e.g., completely immersed) in an aqueous sheath liquid). Thus, in the devices of the invention, one or more of the droplets can be aqueous or comprise an aqueous solution and one or more of the channels can contain a non-aqueous sheath fluid (e.g., a fluorocarbon oil carrier). In either event, the droplets can be well defined in volumes appropriate for the reactions scheduled to occur within the device.

Figure 10:
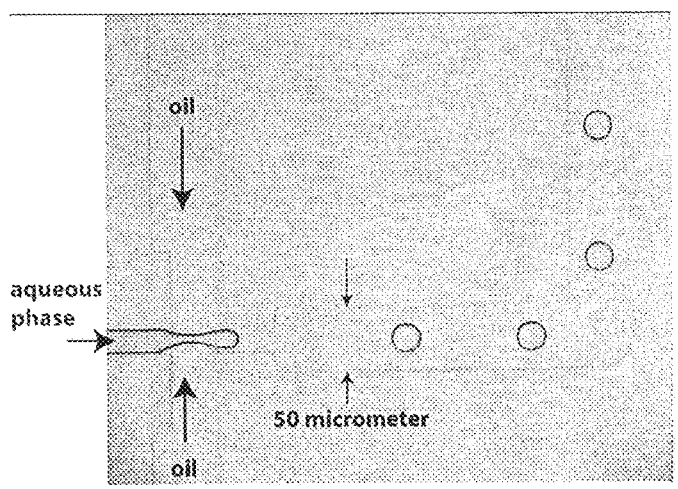
FIG. 10 is an illustration of droplet generation, which can be used with a cell suspension to encapsulate single cells.

A suitable sheath liquid is a fluorinated oil/surfactant mixture (Holtze et al., Lab on a Chip 8(10):1632-1639, 2008 (Raindance Technologies, MA)), which provides excellent drop stability against accidental coalescence and an inert inner droplet surface provided by the PEG block of the surfactant.

Where the analyte is on or within a biological cell, single cells can be encapsulated into aqueous droplets. This step can be performed using the methods described by Weitz and Toner (Lab on a Chip 8(8):1262-1264, 2008) to help overcome stochastic cell loading and increase the likelihood that there is only a single cell in the majority of droplets. More specifically, a cell suspension is guided through a high aspect-ratio microchannel, thereby forcing the cells to flow single-file. As the microchannel terminates, the cells are incorporated into picoliter droplets (approximately 15 pl, corresponding to a cell concentration of $6.times.10.sup.7$ cells/ml). See FIG. 10. The encapsulation process can be facilitated by including a step to help prevent settling (see Cooper and Lee, Lab on a Chip, 2007).

A flow focusing droplet generator can be used to help ensure the generation of monodisperse droplets at very high throughput and in a very robust manner. In this configuration, a liquid flows in a central channel while a second immiscible liquid flows into the two outside channels. The two liquid phases are then forced to flow through a small orifice (nozzle) that is located downstream of the three channels. The outer fluid exerts pressure and viscous stresses that force the inner fluid into a narrow thread, which then breaks inside or downstream of the orifice into droplets. The droplet size is mainly controlled by the dimensions of the nozzle and the flow rates of the liquids.

To help minimize sedimentation of cells (or other analytes) prior to introduction into the present device, one can minimize the length of the introductory tubing and/or its complexity (i.e., the complexity of its shape). Short, straight tubing is best. One can also use a cell stirring system to help minimize sedimentation.

In another "introduction" event, surfactant stabilized aqueous droplets are reinserted into a microfluidic device. See also Baret et al., Lab on a Chip, 2009.

Lysis:

Cell lysis can be achieved (where the sample comprises a cell; the invention is not so limited) by laser techniques, although these may slow the rate of throughput. Where certain cells (e.g., bacterial cells) are encapsulated and analyzed, they may be lysed with heat treatment alone. Lysis can also be induced by combining the cell-containing droplets with approximately 3 nl (or a droplet of 150 μm diameter) of lysis buffer. A number of buffers would be suitable (e.g., 100 mM Tris-HCl, pH 7.5, 500 mM LiCl, 10 mM EDTA, 1% LiDS, 5 mM dithiothreitol (DTT)). Lysis can also be facilitated using an enzyme-based solution such as that developed by Zygem (Hamilton, New Zealand). This method relies on a mix of heat-activated proteases. Preferably, after lysis, the analyte concentration (e.g., genomic DNA concentration) is below 1 mg/ml. After the cell lyses and the cell content solubilizes, genomic DNA de-condenses and will increase the droplet viscosity, which may interfere with the solubilization and mRNA extraction efficiency. After droplet fusion, the larger droplets can be guided through zig-zag channels to ensure mixing and homogenizing of the cell content. Generally, zig-zag channels can be included wherever one wishes to more thoroughly mix the contents of a droplet. If droplet viscosity becomes a problem (clogging, inability to mix and homogenize) DNase I can be included to cut the genomic DNA into smaller fractions.

Two parameters can be used to optimize the conditions of cell lysis inside droplets: (1) cell lysis efficiency and (2) emulsion stability during treatment and upon re-injection. Cell lysis efficiency can be characterized by using different fluorescent markers like calcein-AM that stains the cell cytoplasm, fluorescent wheat germ agglutinin that stains the plasma membrane, or nucleic acid stains like Syto24. After the lysis steps, one can quantify the lysis efficiency by examining the droplets under a fluorescent microscope. The stability of the droplets can be characterized by re-injecting them in a wide and shallow channel, so they are squeezed in a pancake-like shape. Simple algorithms developed under ImageJ can be used to follow the droplet size during the lysis and quantify droplet coalescence.

To verify the lysis process, DNA-binding fluorescent dyes (such as SYBR gold or SYBR green (Invitrogen)) can be included in the lysis buffer. Where lysis occurs, DNA is typically evenly distributed throughout the droplet.

Functionalized Particles:

The functionalized particles useful in the present invention specifically bind the analyte and respond to a field generated within the device. Where the analyte is a nucleic acid sequence, the functionalized particle can include, as an analyte-specific moiety or tag, a nucleotide sequence that is sufficiently complementary to the sequence of the analyte to specifically bind the analyte. In other words, the analyte and the tag can specifically bind one another through base pairing. Where the analyte is an mRNA containing a poly(A) "tail," the tag can include an olig(dT) sequence. Oligo(dT) .sub.25 magnetic beads are commercially available (Dynabead, Invitrogen). For other analytes, the tag can be a chelator or a protein such as an antibody, an analyte-binding fragment or variant thereof, or another type of protein scaffold (e.g., a fibronectin domain).

Based on the bead binding capacity of poly-A mRNA, we estimate requiring approximately 100 magnetic beads per cell or about 15 pl of washed beads (Dynabeads are washed several times in binding buffer (20 mM Tris-HCl, pH 7.5, 1.0 M LiCl, 2 mM EDTA) before use).

Fusion or Coalescence:

Several strategies can be used to fuse droplets in droplet microfluidic devices, including those described here (see, e.g., Ahn et al., Appl. Phys. Lett. 88(26): 264105, 2006, and Christopher et al, Lab on a Chip 9(8):1102-1109, 2009). In the fusion step, two streams of droplets are combined or merge, preferably in a synchronized manner, and fusion occurs by electrocoalescence. When the two droplet streams are combined, the smaller droplet catches up to the bigger droplet until they travel in pairs. After this, the two droplets can be fused by the application of an AC electric field of about 100V (500V/m) at 1 kHz. The applied dielectrophoretic force overcomes the activation barrier posed by the two surfactant stabilized surfaces. This process ensures that there is no accidental coalescence. Synchronization is achieved by controlling the velocities of each incoming stream using a pressure system. The droplet size is controlled by the dimensions of the drop-forming junction and is typically in the range of about 1 pL-10 nL (e.g., 10, 25, 50, or 100 pL, or 0.25, 0.5, 1.0, 2.5, or 5.0 nL).

Alternative Configuration to Achieve Encapsulation and Lysis:

An alternative way to encapsulate and lyse cells is to combine three laminar streams of liquid before droplet formation (see Huebner et al., Chem. Commun. 12:1218-1220, 2007 and Tice et al., Langmuir 19(22):9127-9133, 2003). The middle stream will contain the cells and the outer two streams contain the lysis buffer. Because flow is laminar, the three streams will not mix (except for diffusion) until encapsulated into a droplet. In addition, the lysis buffer can be used to narrow the cell stream and therefore accomplish a high aspect flow dimension that will line up the cells.

Exemplary Configurations:

In one aspect, the invention features microfluidic devices that can be used to separate an analyte from a complex mixture and which can include a substrate comprising a series of contiguous channels and a field generator. The series of contiguous channels can comprise a first channel having an initial segment configured to receive a droplet comprising an analyte that is bound to a functionalized particle (the tagged droplet), a middle segment along which the tagged droplet travels, and a terminal segment that bifurcates into a second channel and a third channel. The field generator is positioned adjacent to the first channel (e.g., adjacent to the middle segment of the first channel) and marginalizes the analyte toward a side of the tagged droplet such that, upon reaching the bifurcation, a portion of the tagged droplet that includes the majority of the analyte enters the second channel and the remainder of the tagged droplet enters the third channel, thereby producing, in the second channel, a smaller droplet that contains the majority of the analyte while excluding at least some of the complex mixture. The series of contiguous channels can further include a fourth channel having an initial segment comprising an opening configured to receive a droplet comprising a solution for diluting the analyte (the dilution droplet), a middle segment along which the dilution droplet travels, and a terminal segment that forms a junction with the second channel. In some embodiments, the devices can also include a series of contiguous channels that further include a fifth channel having an initial segment extending from the junction of the second channel and the fourth channel, the initial segment being configured to receive the smaller droplet from the second channel and the dilution droplet from the fourth channel; a middle segment along which the smaller droplet and the dilution droplet travel and coalesce (the coalesced droplet) and beside which is positioned a field generator; and a terminal segment. The fifth channel can form a junction with the initial segment of the first channel, and the field generator can be positioned beside a segment (e.g., the middle segment) of the fifth channel. This field generator can be the same as the field generator positioned beside the first channel or it can be a distinct field generator. The terminal segment of the fifth channel can bifurcate into a sixth channel and a seventh channel, such that upon reaching the bifurcation, a portion of the coalesced droplet that includes the majority of the analyte enters the sixth channel and the remainder of the coalesced droplet enters the seventh channel, thereby producing, in the sixth channel, a further purified droplet that contains the majority of the analyte while excluding an additional amount of the complex mixture. The field generator positioned beside the fifth channel can be the same as the field generator positioned beside the first channel, or it can be a distinct field generator.

The initial or middle segments of any of the channels (e.g., the fifth channel) can include one or more angular turns to facilitate coalescence of the smaller droplet and the dilution droplet. A part of a channel (e.g., the fifth channel) can also be positioned next to a pair of electrodes capable of supplying an electric field that facilitates coalescence of the smaller droplet and the dilution droplet.

In another aspect, the invention features microfluidic devices that include a microchannel for encapsulating a single cell comprising an analyte in a droplet; and a plurality of channels configured to form junctions (e.g., T-, W-, X-, or Y-shaped junctions) for facilitating continuous, serial separation and dilution of the analyte. As in other instances, these devices can include a field generator and one or more of the other elements or features described herein.

As noted, the invention encompasses compositions and methods for analyzing analytes (e.g., a nucleic acid such as DNA or RNA) in a biological sample, including a single cell. Thus, the invention features microfluidic devices configured to perform single cell mRNA analysis, and these devices can include a series of contiguous channels in a substrate (e.g., an elastomeric material) that define particular zones, as described herein, for analyzing nucleic acids. For example, the devices can include: (1) a first zone in which single cells are placed in aqueous droplets and lysed, thereby generating a cell lysate; (2) a second zone in which microparticles functionalized to specifically bind mRNA are added to the cell lysate, thereby generating microparticle-associated mRNA; (3) a third zone in which the microparticle-associated mRNA is separated from the majority of the remainder of the cell lysate; (4) a fourth zone in which the microparticle-associated mRNA is reverse transcribed into cDNA; and (5) a fifth zone in which the cDNA is amplified with sequence-specific primers. The first zone can include an opening for receiving cells in a suspension; a microchannel, extending from the opening, that is configured to guide the cells in the suspension into single file; a first channel, extending from the microchannel, having an initial segment and a terminal segment, wherein the initial segment, by virtue of being larger than the microchannel, permits each cell to become encapsulated in a single aqueous droplet upon emerging from the microchannel, thereby forming a cell-containing droplet; a second channel having an initial segment and a terminal segment, wherein the initial segment comprises an opening for receiving an aqueous droplet comprising a lysis buffer and the terminal segment of the second channel merges with the terminal segment of the first channel to create a junction; and a third channel extending from the junction of the first channel and the second channel, into which the cell-containing droplet and the droplet comprising a lysis buffer enter and coalesce, thereby generating a droplet comprising a single lysed cell.

The device just described or another other within the invention can also include at least one pair of electrodes (e.g., a pair of electrodes positioned adjacent to the third channel, wherein the electrodes generate an electric field sufficient to destabilize the cell-containing droplet or the droplet comprising a lysis buffer and thereby facilitate the coalescence of the droplets).

The corresponding methods of the invention feature methods of analyzing an analyte in a sample by introducing the sample into a microfluidic device as described herein. For example, the present methods include methods of manipulating an analyte within a sample by: providing the sample; encapsulating the sample within a droplet comprising a functionalized particle, wherein the functionalized particle comprises a field-responsive element and a tag that specifically binds the analyte, thereby generating an analyte-tagged droplet; marginalizing the analyte by exposing the analyte-tagged droplet to a field generator; cleaving the analyte-tagged droplet so the portion of the tagged droplet that includes the majority of the marginalized analyte becomes contained within a smaller droplet; and diluting the analyte by fusing the smaller droplet with a droplet comprising a buffer or reagent, thereby generating an analyte-diluted droplet. The analyte can be a biomolecule (e.g., a nucleic acid (e.g., a DNA or RNA molecule or sequence, including mRNA or a microRNA), protein, sugar, or fat). The single, lysed biological cell can be prepared by encapsulating the cell in a droplet, thereby generating a cell-containing droplet, and fusing the cell-containing droplet with a droplet comprising a lysis buffer (thereby generating a droplet comprising a single, lysed biological cell). The methods can further include the steps of exposing the analyte-diluted droplet to a field generator, wherein the field generator marginalizes the analyte toward a side of the analyte-diluted droplet; and cleaving the analyte-diluted droplet so the portion of the dilution droplet that includes the majority of the analyte becomes contained within a smaller analyte-diluted droplet. One can then further assess the analyte in the analyte-diluted droplet by any method known in the art, including methods that quantitate the analyte. The methods can be carried out in series, repeating the steps with a second sample comprising a second single, lysed biological cell. The second cell can differ from the first cell in that the second cell is more differentiated than the first cell or the second cell may have been exposed to different conditions (e.g., different environmental conditions) than the first cell. Thus, the present methods are amenable to product testing and the like.

Field Generators:

Electrical or magnetic fields, which physically displace the complexes described herein, can be generated in a variety of ways. For example, one can embed a rare-earth magnet (e.g., a 0.125" or 0.187" cube of NdFeB rare earth permanent magnet (Magcraft, Va.)) into the substrate material. Where the substrate comprises PDMS, movement of the magnets can be restricted during the formation of the device by placing an iron metal sheet below the Petri dish containing the silicon wafer and the PDMS. Any of the microfluidic devices of the invention can include, as a magnet as the field generator, in which case the functionalized particle can include a magnetized microsphere. In other embodiments, the field generator can be an electrode emitting an oscillating electric field gradient and the functionalized particle can include a dielectric microsphere. In other embodiments, the field generator can be a focused light or laser beam and the functionalized particle can include a dielectric microsphere.

Magnets and Magnet Placement:

The magnets can either be permanent or electromagnets. In our experiments we used rare earth (NbFeB) magnets of sizes (1/16" or 1/8" or 1/4" square, or 1/8".times.1/8".times.1/4" or 1/8".times.1/8".times.1/2" or 1/4".times.1/4".times.12" or 1/4".times.1/4".times.1" magnetized along the longest dimension). The placement of the magnets should be close to the splitting junction. From 50 micrometer (channel diameter) to several mm from the channel and the placement of the magnet with respect to the junction should be in the range of 3 magnet widths before and after the junction.

It may be desirable to shield some regions of the microfluidic device from the effects of the field generator. This can be readily achieved by incorporation of a shield (e.g., a shield that suppresses the effect of the magnetic field in certain areas of the device). The shield can include nickel, iron, copper, or molybdenum. In other embodiments, the shield is mumetal.

Pressure Control:

Flow control can be achieved by alternative approaches. In one, syringe pumps (Harvard Instruments, MA) can precisely control the flow rates in the channels. The disadvantage of this approach is that low flow rates are hard to achieve and to control; syringe pumps work with linear actuation to push the plunger of a syringe and, in order to reduce flow rates, the syringe volumes need to be reduced. It is difficult to get the samples through the tygon tubing and into the devices if the syringe volumes are smaller than the volumes of the access tubing. The advantage of this approach is that total flow through the system can be accurately set.

In another approach, we have developed a pressure system that controls the pressure of each individual inlet and outlet. It is fed by an air pump that distributes pressured air to 0-30 psi pressure regulators (R 800, Airtrol, WI) attached to individual pressure gauges. Pressure is fed into the top of sealed containers containing liquid samples to push out the liquid into the device through tygon tubing. This pressure system controls the liquid flow inside the devices by setting the pressure difference between inlets and outlets. The pressure controllers can be operated at around 5 psi at the outlet channels, which results in better control over pressure differences. With this approach we can achieve flows of below 0.1 μm/sec in 25 μm.times.25 μm channels. This cannot be achieved with syringe pumps. This capability is especially important when studying in detail the behavior of magnetic particles in droplets under the influence of static magnetic fields.

The pressure system can be linked to a computer and computer controlled, in which case the system can include stepper motors attached to each pressure regulator. These are interfaced with computer controlled stepper motor controllers and can be interfaced with image processing software (e.g., IPLab).

Figure 8:
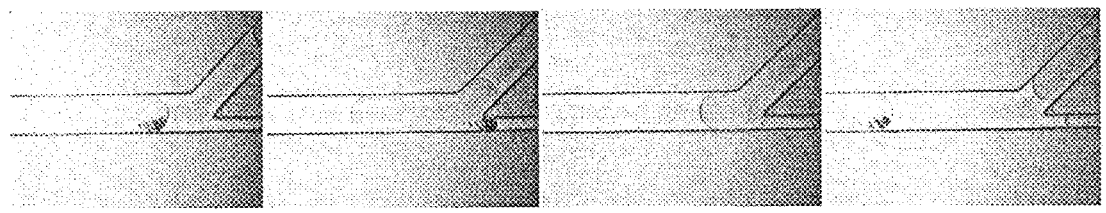
FIG. 8 is a series of photomicrographs showing bead-containing droplets moving through a microfluidic device with a magnet arranged as shown in FIG. 1A. The center of the magnet is placed slightly behind the junction point. The width of the input channel is 50 µm, and the height of the channel is 25 µm. The droplets contained approximately 100 magnetic beads.
Figure 9:
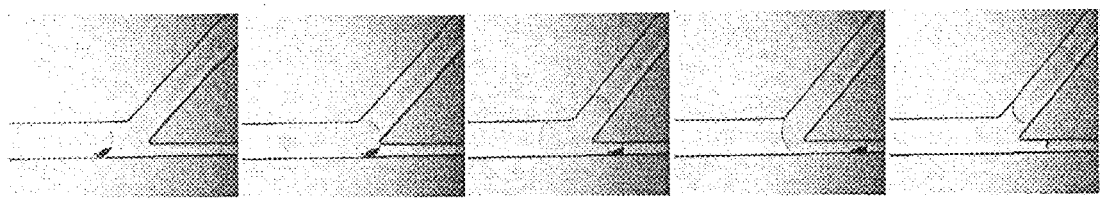
FIG. 9 is a series of photomicrographs showing bead-containing droplets moving through a microfluidic device with a magnet arranged as shown in FIG. 1C. The center of the magnet is placed slightly behind the junction point. The width of the input channel is 50 µm and the height of the channel is 25 µm. The droplets contained approximately 100 magnetic beads.

Sampling and Quality Control:

To extract a certain number of droplets for sampling during the course of a reaction, droplets can be deflected into a channel for collection (see FIG. 8 and Baret et al., Lab on a Chip, 2009). For example, dielectrophoresis can be used to deflect aqueous droplets from one channel to another. Details of making and connecting the electrodes are given in Example 3. Image processing can be used to control the voltage supply to extract the desired number of droplets for analysis.

RT-PCR:

Recently, it has been shown that quantitative polymerase chain reaction (qPCR) and reverse transcription PCR(RT-PCR) can be performed in pL droplets (Beer et al., Anal. Chem. 79(22):8471-8475, 2007 and Beer et al., Anal. Chem. 80(6):1854-1858, 2008). It has also been shown that, when using droplet microfluidics, qPCR can be performed in a continuous way (Kiss et al., Anal. Chem., 2008 and Schaerli et al., Anal. Chem. 81(1):302-306, 2009) by using a long serpentine channel shuttling droplets between two different temperatures for denaturation, extension, and relaxation steps. These processes can be carried out in the present devices to amplify nucleic acids from single cells. Accordingly, the microfluidic device of the present invention can include a serpentine channel that shuttles droplets between different temperature zones.

The droplets containing magnetic beads with hybridized mRNA and RT-PCR mix can be injected on one side and flown through a temperature zone of 42-50.degree. C. to synthesize the first cDNA strand using a reverse transcriptase (this process takes about 15 minutes). Then the droplets will undergo a 35 step PCR reaction. The reverse transcriptase is irreversibly inactivated by the first pass through the 95.degree. C. zone. Observation points can be inserted at every other PCR repeat (67.degree. C. zone) to measure SYBR green fluorescence to determine the amount of amplification product.

The flow rate through the device is given by the timing of the PCR reaction. The denaturation step can be carried out at 95.degree. C. for 15 seconds and an elongation, relaxation step can be carried out at 67.degree. C. for 40 seconds. Taking into account the dimensions of the chip, a flow speed of 2 mm/sec is necessary.

The mRNA extraction and concentrating steps may dictate flow rates that are orders of magnitude lower than the flow rates required by the RT-PCR step. To help reconcile these rates, one can inject more sheath liquid (e.g., oil) into the flow and therefore speed up the droplets. As noted above, isolating the analyte and performing other steps, such as PCR, can also be carried out in two separate devices.

To help ensure that the mRNA is not degraded by RNases, all buffers can be prepared RNAse free (e.g., by treating water with 0.1% diethylpyrocarbonate (DEPC) with subsequent autoclaving).

Temperature control can be achieved by using several Watlow SD31 temperature controllers (Watlow) attached to PDMS embedded 1 mm.times.1 mm RTDs (Omega) and custom flexible silicon strip heaters (Watlow) that are bonded to the bottom of the cover glass. For RT-PCR, a section of the device is heated to 37.degree. C. (for first strand c-DNA synthesis) and to 95.degree. C. and 65.degree. C. in sections for the qPCR section. The temperature distribution can be verified using Rhodamine-B life time measurements (see Schaerli et al., Anal. Chem. 81(1):302-306, 2009).

Designated Zones:

The present devices can be described as having zones in which different events occur or different reactions are carried out. For example, where the analyte is a biomolecule, the device can include: (1) a first zone in which single cells are placed in droplets (e.g., aqueous droplets) and lysed, thereby generating a cell lysate; (2) a second zone in which functionalized particles are added to the cell lysate, thereby generating particle-associated mRNA; (3) a third zone in which the particle-associated mRNA is separated from the majority of the remainder of the cell lysate; (4) a fourth zone in which the particle-associated mRNA is reverse transcribed into cDNA; and (5) a fifth zone in which the cDNA is amplified with sequence-specific primers.

In this configuration, the channels within at least the first three zones can be configured as described herein to isolate an analyte by splitting a droplet in which it is marginally contained at a Y- or T junction and to subsequently redilute the isolated analyte with buffer or another material by allowing the droplet containing the isolated analyte to fuse or coalesce with a droplet containing the buffer or other material. PCR can be performed within the device by flowing the droplets through relatively long serpentines that shuttle between two temperature zones (e.g., 95.degree. C. and 67.degree. C.). The amplification can be monitored and ultimately assessed by examining a fluorescent signal.

While there are advantages to performing as many steps as possible within the same device, alternatives are possible. For example, after polymerization of the first strand of cDNA (e.g., at 42-50.degree. for 30 minutes), after which the chemical composition within the droplets is more stable, it is possible to collect the droplets (e.g., several thousand droplets) in a container (e.g., an Eppendorf tube). The collected droplets can then be placed in a thermal cycler for PCR, beginning with a hot start (e.g., 95.degree. C. for 15 minutes) to deactivate the reverse transcriptase). After the PCR has been performed, the reaction mixture (initially formed by the collected droplets) can be reintroduced into an analysis droplet microfluidic chip that will measure the fluorescence of each drop. With this procedure, using molecular beacons as fluorescent probes, gene expression of several genes can be measured simultaneously.

In corresponding methods, the invention features processes for isolating and analyzing a biomolecule. The methods can include the steps of: (1) providing a single cell within a droplet (e.g., aqueous droplet and lysing the cell, thereby generating a cell lysate; (2) exposing the cell lysate to a functionalized particle for a time and under conditions sufficient to permit the biomolecule (e.g., an mRNA or microRNA) to become associated with the particle; and (3) separating the particle-associated biomolecule from the cell lysate. Where the biomolecule is an mRNA (or microRNA), the methods can further include the steps of performing reverse transcription to produce cDNA from the mRNA (or microRNA) and amplifying the cDNA with sequence-specific primers. The cDNA can then be transferred to a sequencer or quantitated to determine the expression level of the mRNA (or microRNA).

Kits:

Microfluidic devices with one or more of the features described herein, including devices configured to generate cDNA libraries from, for example, single biological cells, can be packaged together with instructions for use as a kit. Accordingly, the invention features such kits, including those limited to essentially, the device, instructions for use, and packaging, as well as those that include one or more of the following items: (a) a fluid for encapsulating a sample comprising an analyte in a droplet (which may be aqueous or non-aqueous); (b) a fluid for sheathing the droplet (which may be aqueous or non-aqueous); (c) a lysis buffer; (d) a functionalized particle; (e) a dilution buffer; and (f) a solution comprising a reagent. As noted, the device can be any device described herein, including those that further include a microchannel for encapsulating a single cell comprising an analyte in a droplet and/or a field generator. Where the fluid for encapsuling the sample is aquous, the fluid for ensheathing the droplet can be non-aqueous, and vice versa. The functionalized particles included with the kit can include a microsphere or nanotube assembly, and a tag for a nucleic acid (e.g., an oligo(dT) tag or an oligonucleotide that is sufficiently complementary to the sequence of an RNA (e.g., an mRNA or microRNA) to specifically bind the RNA) or protein (e.g., an antibody or other protein scaffold) can also be included. Optional reagents include enzymes (e.g., a reverse transcriptase or a polymerase). The reagents can also be any other enzyme, substance, or buffer useful in carrying out PCR (e.g., an oligonucleotide primer).

In the Examples below, we describe additional techniques to concentrate, extract and process functionalized particles in droplet microfluidics devices.

EXAMPLES

Example 1

As noted, the microfluidic devices of the present invention can be fabricated using standard techniques (e.g., standard soft-lithography techniques). By way of example, we cleaned a 3" silicon wafer in RCA1 and RCA2 to remove, respectively, essentially all organic and inorganic residues, and subsequently dehydrated the wafer at 200.degree. C. for 15 minutes to fully dry it. A 25 µm layer of SU-8 (Microchem) was cast on the silicon wafer by spin coating the resist at 3500 rpm for 30 seconds (Laurell). The wafer was then baked for 10 minutes at 60.degree. C., 80.degree. C., and 95.degree. C., consecutively, to fully cure the SU-8. The wafers were exposed to UV light (Newport) through a photolithography mask containing the desired channel geometry (CAD/Art Services) and subsequently developed in SU-8 developer (Microchem). To clean the wafer and stop the developing process, it was dipped in isopropyl alcohol, rinsed with DI water, and blown dry with argon gas. The wafer was then hard baked for 5 minutes at 200.degree. C. to further strengthen the channels. The completed wafer was silanized by placing it next to a drop of tridecafluoro-1 1 2 2-tetrahydrooctyl-1-trichlorosilane on a glass petri dish in a dessicator that was evacuated for two hours.

To form the chip itself, a 10:1 (w/w) mixture of poly(dimethylsiloxane) (PDMS) to cross linker (Sylgard 184) was mixed and poured over the wafer containing the SU-8 mold. The chip was subsequently degassed in a dessicator for one hour and cured at 95.degree. C. for one hour.

Once cured, the chip was peeled from the wafer and cut to size before access holes were drilled with a 24 gauge steel punch. The access channels were subsequently blown with argon gas to remove any PDMS debris that was left behind. The chip and a new 1".times.3" microscope slide were cleaned by sonication in three successive solutions: 2% Hellmanex.™ .solution, DI water, and methanol, each for 10 minutes. Both the chip and the microscope slide were then dried with argon and placed in a plasma cleaner which was evacuated for 10 minutes to ensure full dehydration of the chip and glass. The chip and slide were subsequently exposed to oxygen plasma at 1 torr for 1 minute (Harrick Plasma PDC 326) and immediately bonded. The completed device was placed on a hotplate at 70.degree. C. for 10 minutes to remove any trapped air bubbles and to ensure complete bonding of the PDMS to the glass.

In order to make the channels fully hydrophobic and ensure that the walls were wet only with the sheath fluid, the channels were treated with a 2% silane (Helptadecafluoro-1,1,2,2-tetrahydrodecyl)trichlorosilane from Gelest) solution in fluorinated oil (FC 40) and subsequently flushed with copious amounts of pure fluorinated oil to ensure removal of excess silane residue. The silane solution and fluorinated oils were pushed through the microfluidics devices using a 1 ml glass syringe with volumes of 20 µL and 200 µL respectively.

The droplet manipulation experiments performed employed two distinct microfluidics chips used for droplet formation and bead concentration and droplet fission respectively. The droplets containing magnetic beads were created using a microfluidics chip containing a simple flow focusing geometry. In order to maintain consistent bead concentrations, a small volume of mixed bead solution (50 µL) was aspirated into a length of 24 gauge Teflon® tubing. This tubing was connected to a syringe containing HFE 7500 (3M), a fluorinated oil, which did not mix with the magnetic bead solution. This syringe was subsequently pushed via an automatic syringe pump, thus injecting the magnetic bead solution into the microfluidics chip at a constant volumetric flow rate. The flow rate for the magnetic bead solution was set to 5 µL/min whereas the sheath liquid was set at 10 µL/min. In this case, the sheath liquid was a fluorinated oil, HFE 7500 containing 2% EA surfactant (Raindance Technologies). With these conditions, it took roughly 10 minutes to change all of the 50 of magnetic bead solution into 50 µm diameter, monodisperse droplets. This droplet formation was completed with magnetic bead solution concentrations of 5 mg/ml and 1 mg/ml.

The droplets containing the magnetic bead solution were subsequently collected from the outlet of the droplet formation chip and re-aspirated into another length of Teflon® tubing for re-injection into the magnetic manipulation and droplet fission chip. The droplets were also pushed with an automatic syringe pump with fluorinated oil as a sheath liquid to control the frequency of the droplets entering the chip. Ideal droplet entry conditions were established with volumetric flow rates of 0.030 µL and 0.015 µL for the sheath liquid and the droplet solution respectively.

For the magnetic manipulation chip, the magnetic field was established by placing rare earth magnets directly adjacent to the microfluidic channels just at the point of bifurcation where the droplets split. In this case, the magnets were placed by manually cutting ports in the PDMS chips roughly 1.5 mm from the main channel.

As these droplet plugs advanced downstream, the beads began to enter stronger magnetic field gradients. Initially the beads began to conglomerate forming large groupings as opposed to remaining dispersed individually throughout the droplet. These conglomerations of beads subsequently began to align with the magnetic field lines until there were no individual beads remaining in the droplet. Once fully conglomerated, the bead groupings migrated towards the magnet and ultimately became concentrated essentially completely on one side of the droplet. Once concentrated, these beads were split at a Y junction with one channel having a diameter of 40 µm and the other a diameter of 10 µm. This unequal division allowed for the formation of droplets with different volumes. By positioning the magnet on the side of the channel with the smaller Y junction split we were able to isolate essentially all of the magnetic beads within a droplet plug into a smaller volume and split this volume into a more concentrated new droplet. In the absence of the magnetic field, the droplets split as expected but the magnetic beads showed no clear bias to either of the two Y junction channels. With a magnet in place, however, the beads clearly migrated and were thus concentrated into new, smaller droplets.

Example 2

To optimize the extraction of a specific analyte, we strive to maintain a consistent magnetic bead concentration within each droplet. A consistent concentration helps to ensure that there will be enough beads to bind all of the targeted material. It is important that this binding is consistent for highly sensitive studies, especially those involving genetic material from single cells, where a slight alteration in binding, or a lack of binding, may lead to variations in the integrity of the analysis.

Droplets containing magnetic beads were created using a microfluidics chip containing a simple flow focusing geometry. In order to maintain consistent bead concentrations, a small volume of mixed bead solution (50 µL) was aspirated into a length of 24 gauge Teflon® tubing. This tubing was connected to a syringe containing HFE 7500, a fluorinated oil, which did not mix with the magnetic bead solution. This syringe was subsequently pushed via an automatic syringe pump, thus injecting the magnetic bead solution into the microfluidics chip at a constant volumetric flow rate. The flow rate for the magnetic bead solution was set to 5 µL/min whereas the sheath liquid, HFE 7500, was set at 10 µL/min. With these conditions it took roughly 10 minutes to change all of the 50 µL of magnetic bead solution into 50 µm diameter, monodisperse droplets. This droplet formation was completed with magnetic bead solution concentrations of 5 mg/ml and 1 mg/ml.

In order to verify the magnetic bead concentration within these droplets, a test volume of roughly 5 µL of the droplets was placed between two cover slips such that the droplets were flattened and all of the beads were visible in one focus plane. With images collected with a microscope-mounted camera, it was then possible to analyze the beads within the droplets. The number of beads within each droplet was measured using the particle analyzer function of Image-J. Droplets from both the 5 mg/ml and 1 mg/ml solutions were analyzed in such a fashion.

Figure 5A:
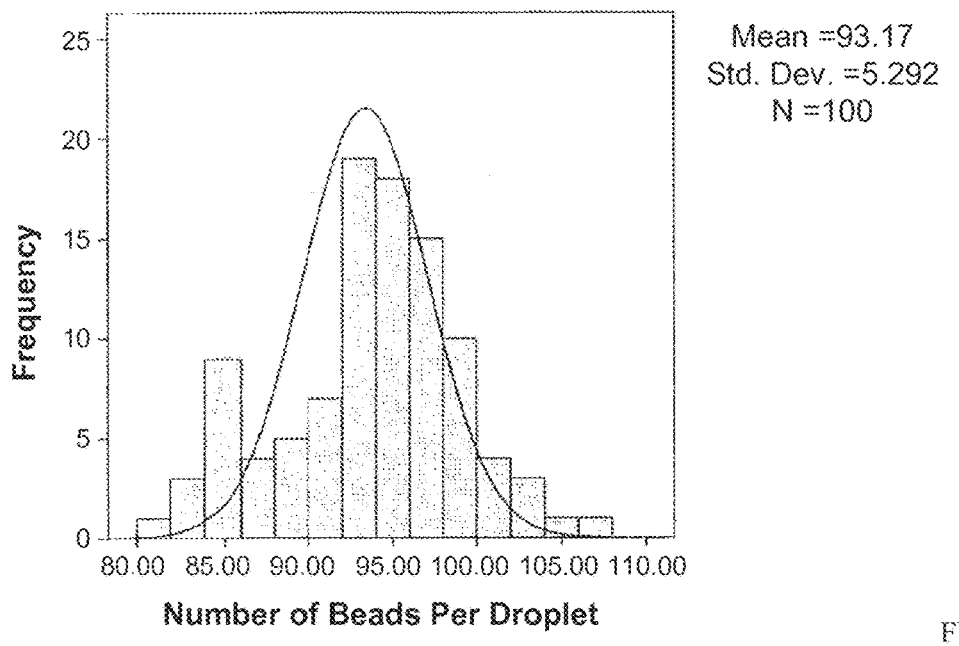
FIG. 5A and FIG. 5B are graphs illustrating the frequency of the number of beads per droplet produced under the conditions of Example 2.
Figure 5B:
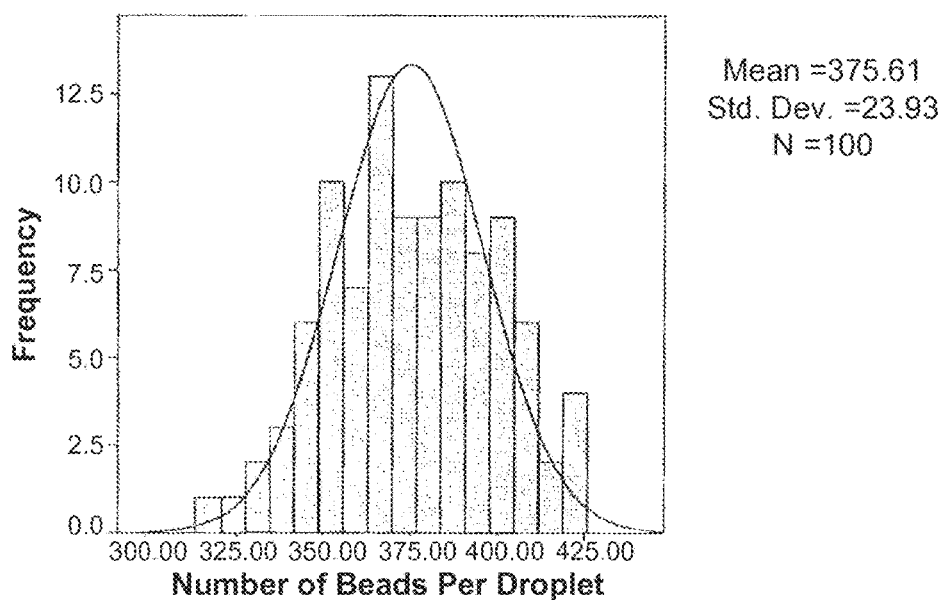

Analysis of both the droplets containing a 1 mg/ml solution of magnetic beads and a 5 mg/ml solution revealed fairly normally distributed concentrations of beads per individual droplet (FIG. 5A and FIG. 5B). The droplets containing the 1 mg/ml solution had a mean bead count of 93.17 with a standard deviation of 5.292. This amounts to a coefficient of variation of 0.057 or 5.7%. The droplets containing the 5 mg/ml solution presented a coefficient of variation of 0.064 or 6.4% based on a mean bead count of 375.61 and a standard deviation of 23.93.

Example 3

Figure 6:
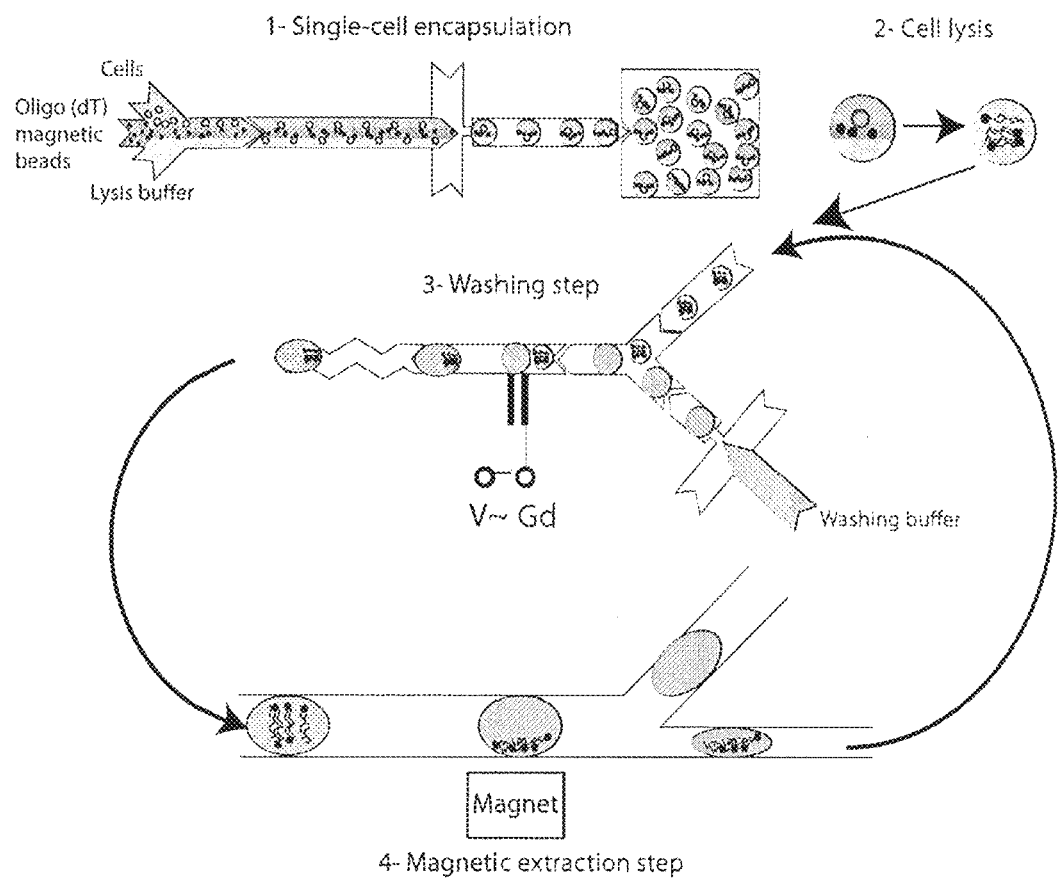
FIG. 6 is a schematic workflow for the creation of single cell cDNA libraries in droplets. In (1), single cells are co-encapsulated in droplets with heat activated cell lysis buffer (ZYGEM) and Oligo (dT)25 magnetic microbeads. In (2), cell lysis is achieved (5 minutes at 75.degree. C.). In (3), the droplets are reinjected into a "chip" (a microfluidic device) to be combined with washing buffer by electrocoalescence. In (4), the magnetic beads are extracted and concentrated into a smaller droplet. Steps (3) and (4) are repeated to provide washing and to change buffers for reverse transcription.
Figure 7:
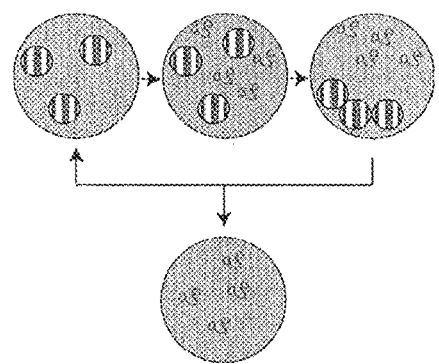
FIG. 7 is a schematic illustrating the use of cDNA libraries in droplets. The striped spheres represent the single cell cDNA library. In the next droplet, a PCR amplification releases free DNA copies. The beads are then separated from the DNA to recover the original library and a droplet filled with DNA for further analysis. This method can be used to probe a series of single genes or group of genes.

The devices and methods of the invention enable the creation of single-cell cDNA libraries that are covalently bound to magnetic microparticles inside droplets. The whole workflow comprises four steps that are depicted in FIG. 6. Throughout this protocol we will use three individual microfluidics chips: (1) single-cell encapsulation chip; (2) a droplet reinsertion and fusion chip to dilute the droplet's content with a washing buffer; and (3) a magnetic separation chip. Each chip is run in sequence and the outputs (droplets) are collected in tubes.

Once the cDNA single-cell library is prepared, the mRNAs will be reverse-transcribed by merging the cDNA droplets with droplets containing a reverse-transcription (RT) solution (MessageSensor RT-Kit, Ambion). After collection the droplets will be incubated at 42.degree. C. for 30 minutes for triggering the cDNA synthesis and at 95.degree. C. for 15 minutes to deactivate the reverse transcriptase. We can measure the efficiency of the RT by quantifying the level of specific cDNAs by qPCR after pooling a specific volume of droplets. The droplet workflow can be compared to the bulk approach.

The final product is a collection of covalently bound single cell cDNA libraries in individual droplets. Because the library is bound to magnetic particles, the library can be re-used by amplifying specific cDNAs (selected by PCR primers) using a few PCR cycles (Lee, Analyt. Biochem. 206:206-207, 1992). The cDNA library will be recovered by simply separating the magnetic beads from the amplified DNA using our method. The separation step will regenerate the initial cDNA library that can be re-used. The aqueous cDNA libraries will be subsequently used for studying the expression level of specific genes in individual droplets using quantitative PCR. More complicated schemes can be designed in which the identity of the cell is maintained while creating individual gene droplets. For example, individual droplets can be sequentially stored in an array before performing quantitative-PCR (qPCR) (Boukellal et al., Lab on a Chip, 9:331-338, 2009; Schmitz et al., Lab on a Chip, 9:44-49, 2009).

Another exciting outcome is the identification of genetic signatures or gene profiles in rare cells that lack specific surface markers. For example, the present methods can be used to analyze circulating tumor cells (CTCs) that are present in blood at a 1:10.sup.9 ratio (Stott et al., Sci. Transl. Med. 2:25ra3, 2010; Maheswaran and Haber, Curr. Opin. Genet. Dev. 20:96-99, 2010). Even with a million fold enrichment using collagen adhesion matrix technology (Lu et al., Int. J. Cancer, 126:669-683, 2010; Fan et al., Gynecol. Oncol. 112:186-191, 2009; Paris et al., Cancer Lett. 277: 164-173, 2009), one is still faced with a lower than 1:1000 ratio of rare cells. Our technology can be used to create single cell cDNA libraries and such libraries, including those in which the cDNA is still attached to a functionalized particle (e.g., a magnetic bead), are within the scope of the present invention. The cells can be already enriched cells encapsulated in droplets, and the droplets can be sorted according to the expression of a specific CTC marker gene (e.g., as measured by PCR). After having collected enough cells (e.g., CTCs), global gene expression methods can be applied (e.g. gene chip, or next generation sequencing).

What is claimed is:

1. A method of amplifying a target polynucleotide in a biological sample comprising:
    a) placing a single cell in an aqueous droplet;
    b) lysing the single cell, thereby generating a cell lysate;
    c) reacting the cell lysate with a tag attached to a bead, thereby binding the target polynucleotide to the tag;
    d) moving the bead into a reaction zone or a container by using an electrical or magnetic field; and
    e) amplifying the target polynucleotide.

2. The method of claim 1, wherein the target polynucleotide comprises an mRNA molecule and the tag comprises a polynucleotide sequence complementary to the target polynucleotide.

3. The method of claim 2, wherein the tag comprises oligo(dT).

4. The method of claim 2, wherein the step of amplifying comprises RT-PCR.

5. The method of claim 1, wherein the target polynucleotide comprises a DNA molecule and the tag comprises a polynucleotide sequence complementary to the target polynucleotide.

6. The method of claim 1, wherein the step of lysing comprises reacting the single cell with lysis buffer.

7. The method of claim 1, wherein the method is performed in a microfluidic device.

8. The method of claim 7, wherein the microfluidic device comprises contiguous channels.

9. The method of claim 1, wherein the bead comprises a magnetic particle.

10. A method of amplifying a target polynucleotide in a biological sample comprising:
    a) placing a single cell in an aqueous droplet;
    b) lysing the single cell, thereby generating a cell lysate;
    c) reacting the cell lysate with a tag attached to a bead, thereby binding the target polynucleotide to the tag, wherein the tag comprises oligo(dT);

d) moving the bead into a reaction zone or a container; and e) amplifying the target polynucleotide.

11. A method of amplifying a target polynucleotide in a biological sample comprising:
   a) placing a single cell in an aqueous droplet;
   b) lysing the single cell, thereby generating a cell lysate;
   c) reacting the cell lysate with a tag attached to a bead, thereby binding the target polynucleotide to the tag;
   d) moving the bead into a reaction zone or a container; and
   e) amplifying the target polynucleotide by RT-PCR.

\* \* \* \* \*